(12) United States Patent
Thijs et al.

(10) Patent No.: US 8,150,489 B2
(45) Date of Patent: Apr. 3, 2012

(54) SYSTEM AND METHOD FOR MEASURING BIOELECTRICAL SIGNALS OF A USER

(75) Inventors: Jeroen Adrianus Johannes Thijs, Aachen (DE); Olaf Such, Aachen (DE); Jens Muehlsteff, Aachen (DE); Harald Reiter, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 935 days.

(21) Appl. No.: 11/911,826

(22) PCT Filed: Apr. 4, 2006

(86) PCT No.: PCT/IB2006/051023
§ 371 (c)(1), (2), (4) Date: Oct. 18, 2007

(87) PCT Pub. No.: WO2006/111876
PCT Pub. Date: Oct. 26, 2006

(65) Prior Publication Data
US 2008/0208028 A1    Aug. 28, 2008

(30) Foreign Application Priority Data
Apr. 19, 2005 (EP) .................................. 05103132

(51) Int. Cl.
*A61B 5/04* (2006.01)
*A61B 5/0402* (2006.01)
*A61B 5/0428* (2006.01)

(52) U.S. Cl. .......................... 600/372; 600/393; 600/509

(58) Field of Classification Search .................. 600/372, 600/509; 606/129
See application file for complete search history.

(56) References Cited

U.S. PATENT DOCUMENTS

| | | | |
|---|---|---|---|
| 4,263,919 A | 4/1981 | Levin | |
| 5,795,293 A | 8/1998 | Carim et al. | |
| 6,366,803 B1 | 4/2002 | Fee | |
| 6,974,419 B1 * | 12/2005 | Voss et al. | 600/485 |
| 6,993,379 B1 * | 1/2006 | Kroll et al. | 600/510 |
| 2004/0254437 A1 | 12/2004 | Hauck et al. | |

FOREIGN PATENT DOCUMENTS

| | | |
|---|---|---|
| WO | 2004052190 A1 | 6/2004 |
| WO | 2004000115 A1 | 12/2004 |
| WO | 2004110268 A1 | 12/2004 |

OTHER PUBLICATIONS

Hamilton, P. S., et al.; Comparison of Methods for Adaptive Removal of Motion Artifact; 2000; Computers in Cardiology; 27:383-386.

(Continued)

*Primary Examiner* — Lee Cohen
*Assistant Examiner* — Erin M Cardinal

(57) ABSTRACT

The invention relates to a system and method for measuring bioelectrical signals of a user. Furthermore the invention relates to a computer program for measuring bioelectrical signals of a user. In order to provide a technique for measuring bioelectrical signals with reduced motion artefacts a new method is provided, comprising the steps of determining the displacement of an electrode, the electrode being adapted for measuring a bioelectrical signal, and adjusting the position of said electrode depending on the determined displacement. The present invention can be used in any system for measuring bioelectrical signals, which uses electrodes, e.g. in any ECG measurement system. With the reduction of artefacts according to the present invention the performance of all those systems can be substantially increased.

11 Claims, 3 Drawing Sheets

OTHER PUBLICATIONS

Figure 1:
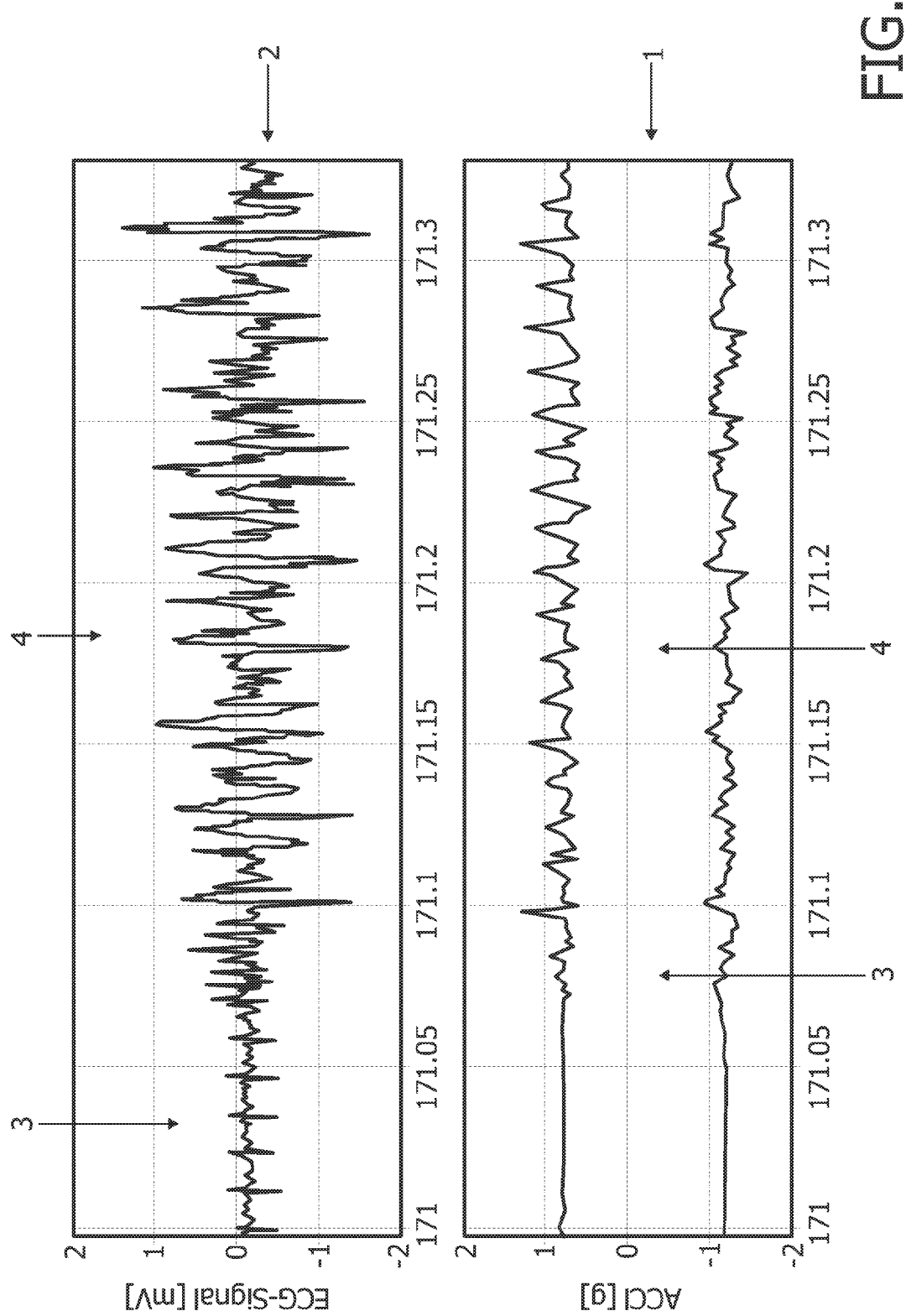

Hamilton, P. S., et al.; Adaptive Removal of Motion Artifact; 1997; IEEE/EMBS; 19:297-299.

Raya, M.D., et al.; Adaptive Noise Cancelling of Motion Artifact in Stress ECG Signals Using Accelerometer; 2002; IEEE/BMES; 2:1756-1757.

Luo, S., et al.; Experimental Study: Brachial Motion Artifact Reduction in the ECG; 1995; IEEE-Computers in Cardiology; pp. 33-36.

Tong, D. A., et al.; Adaptive Reduction of Motion Artifact in the Electrocardiogram; 2002; IEEE/EMBS/BMES; pp. 1403-1404.

* cited by examiner

SYSTEM AND METHOD FOR MEASURING BIOELECTRICAL SIGNALS OF A USER

The invention relates to a system and method for measuring bioelectrical signals of a user. Furthermore the invention relates to a computer program for measuring bioelectrical signals of a user.

Bioelectrical signals, including bioelectrical potentials and/or bioelectrical currents, are monitored and recorded using skin-mounted electrodes to assist in the diagnosis and treatment of many different medical illnesses and conditions.

One example of a bioelectrical signal monitored using such electrodes is the electrical activity of the heart recorded in the form of an electrocardiogram (ECG). ECG measurements using skin-mounted electrodes are a common way of analyzing the cardiac function of a subject. The ECG provides valuable information on heart rate, rhythm changes and heart conditions. Usually some sort of electrolyte is provided between the skin and the electrode. If dry electrodes are employed, sweat is used as an electrolyte. The voltage that is measured across an electrode pair is the difference between the individual half cell potentials that are established by the diffusion of ions into the electrolyte and is called a lead. Measuring several leads provides several projections of the heart's potential vector, making up the ECG.

A big problem with ECG measurements are motion artefacts. Every change in the relative position of an electrode to the skin disturbs the equilibrium underneath the electrode resulting in a rather large change of the half cell potential. This potential results in a large disturbance of the ECG which can be as big as ten times the original ECG signal. Several methods for reducing the occurrence of motion artefacts are known. Increasing electrode pressure on the skin makes the electrode position less susceptible to movements but also decreases the wearing comfort of electrodes. Another approach is to lower the skin-electrode resistance to reduce the artefact sensitivity. An overview on methods to reduce artefacts is given by the U.S. Pat. No. 5,795,293.

It is an object of the present invention to provide a technique for measuring bioelectrical signals with reduced motion artefacts.

This object is achieved according to the invention by a method of measuring bioelectrical signals of a user, comprising the steps of determining the displacement of an electrode, the electrode being adapted for measuring a bioelectrical signal, and adjusting the position of said electrode depending on the determined displacement.

This object is also achieved according to the invention by a system for measuring bioelectrical signals of a user, comprising a determination unit adapted for determining the displacement of an electrode, the electrode being adapted for measuring a bioelectrical signal, and an adjusting unit adapted for adjusting the position of said electrode depending on the determined displacement.

This object is also achieved according to the invention by a computer program, comprising computer program instructions to determine the displacement of an electrode depending on an input signal, the electrode being adapted for measuring a bioelectrical signal, and computer program instructions to generate an output signal for adjusting the position of said electrode depending on the determined displacement, when the computer program is executed in a computer. The technical effects necessary according to the invention can thus be realized on the basis of the instructions of the computer program in accordance with the invention. Such a computer program can be stored on a carrier or it can be available over the internet or another computer network. Prior to executing the computer program is loaded into a computer by reading the computer program from the carrier, for example by means of a CD-ROM player, or from the internet, and storing it in the memory of the computer. The computer includes inter alia a central processor unit (CPU), a bus system, memory means, e.g. RAM or ROM etc. and input/output units.

In contrast to the prior art, where in a first step the signal is measured and in a subsequent step an artefact detection and an artefact compensation is carried out, a basic idea of the present invention is to control the impact of artefacts before or during measurement. In other words, the direct cause of a possible artefact is detected in a first step and the measuring process is adapted in order to reduce the influence of the cause on the measurement subsequently. Then, in a next step the actual measurement is carried out. In contrast to the prior art, where artefact reduction is carried out always in an passive way, the present invention suggests to actively reduce motion artefacts using a control system that continuously adjusts the electrode position or measurement to minimize artefacts.

The present invention can be used in any system for measuring bioelectrical signals, which uses electrodes, e.g. in any ECG measurement system. With the reduction of artefacts according to the present invention the performance of all those systems can be substantially increased.

These and other aspects of the invention will be further elaborated on the basis of the following embodiments, which are defined in the dependent claims.

Preferably the displacement of the electrode is determined by determining a motion. For this purpose the determination unit preferably comprises an accelerometer. Preferably an accelerometer is used, which is adapted for measuring acceleration in several directions.

Movement data is continuously monitored and analysed and the resulting electrode displacement is determined using an appropriate analysing model. In a subsequent step the position of the electrode is adjusted depending on the displacement determined. Preferably the measuring position of the electrode is really or virtually moved in the opposite direction of the displacement, to compensate for the displacement.

According to a first embodiment of the invention the motion of the user is determined by an accelerometer, which is arranged remotely from the electrode. If the accelerometer is positioned in a close vicinity of the electrode, the acceleration of the electrode relative to an acceleration measured in close vicinity can be estimated. Subsequently the change of half cell potential is determined by modelling the effect of an acceleration in the vicinity of the electrode to the electrode displacement.

According to a second embodiment of the invention the motion of the electrode relative to the user is determined by an accelerometer. In this case the accelerometer and the electrode preferably form a motional unit. In other words, the accelerometer is integrated into the electrode or positioned on the electrode, e.g. on top of the electrode, such that the accelerometer determines the motion of the electrode. Preferably a second accelerometer is arranged remotely from the electrode. The second accelerometer determines the motion of the user. In this case the difference in acceleration between electrode and the user's body provides the displacement of the electrode. In all cases a fast control system is provided. The control system uses the accelerometer data as input signal and generates a control signal (output signal) for compensating the electrode's displacement based on the electrode displacement data as input.

According to a third embodiment of the invention an electrode arrangement is used, which comprises a number of adjacent electrode areas, each area being adapted for measuring a bioelectrical signal. For this purpose a single electrode may be used, which comprises a number of separated electrode areas, which are electrically isolated from each other. Alternatively a number of electrodes are used in order to form the electrode arrangement, wherein each single electrode serves as an isolated electrode area of the electrode arrangement. For obtaining a sufficient resolution preferably four or more electrode areas are provided, such that at least one electrode area is provided for each main direction "up", "down", "left", and "right". Subsequently an impedance distribution is determined by comparing the impedance of the different electrode areas. For this purpose an impedance measurement is carried out by injecting current through the electrodes and measuring the resulting voltage. A change in the impedance distribution indicates a displacement of the electrode or the electrode arrangement respectively.

After the displacement of the electrode is determined, the position of the electrode or electrode arrangement is adjusted. Preferably the real position of the electrode is adjusted, e.g. by means of an actuating element for moving the electrode. The actuating element may comprise a small motor. The adjusting of the electrode's displacement by means of an actuating element, thereby forming a closed-loop control system, may be applied for all embodiments described above.

In case of the third embodiment preferably the virtual measuring position, i.e. the center of measurement of the electrode arrangement, is adjusted. For this purpose the displacement of the electrode areas is determined by measuring an impedance distribution over the number of electrode areas. Subsequently the virtual measuring position of the electrode is adjusted accordingly. In other words, the measuring data derived from the arrangement of electrode areas are used to compensate for the displacement of the electrodes. Preferably this is carried out by virtually moving the center of the measurement from the absolute center of the electrode towards the direction of the displacement. This is accomplished by using a weighted mix of the different electrode areas. The weights are obtained from the impedance measurements.

Figure 2:
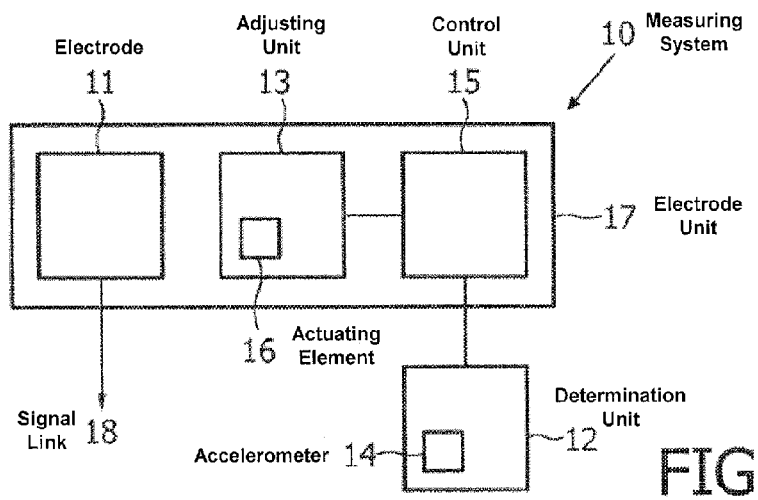
Figure 3:
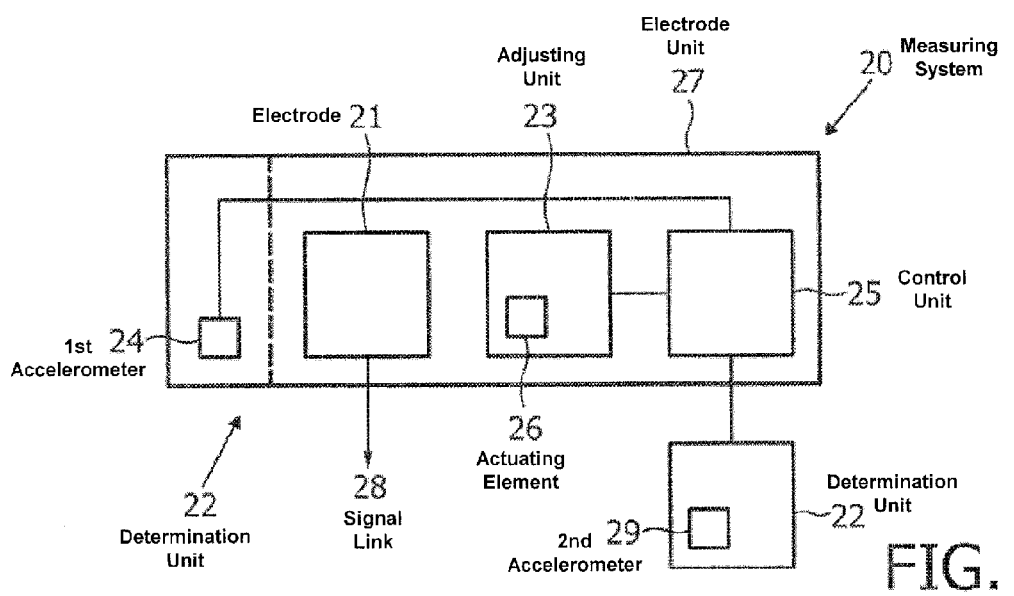
Figure 4:
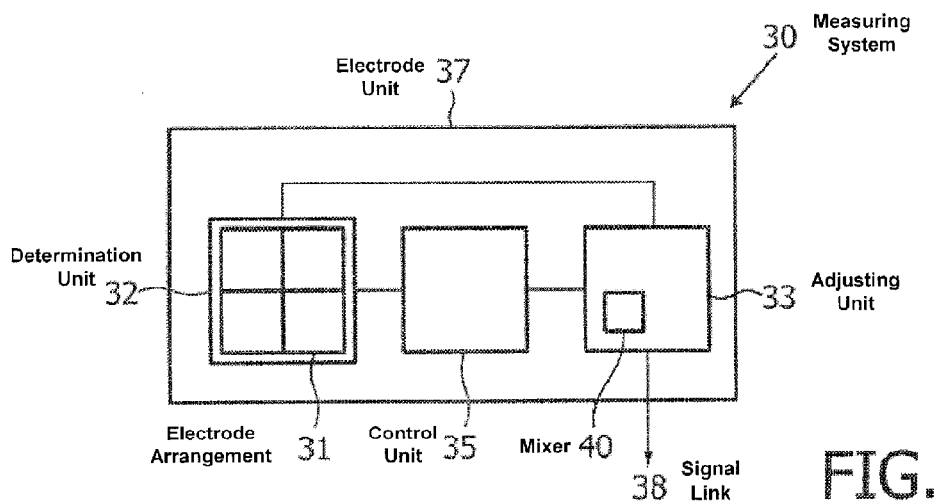
Figure 5:
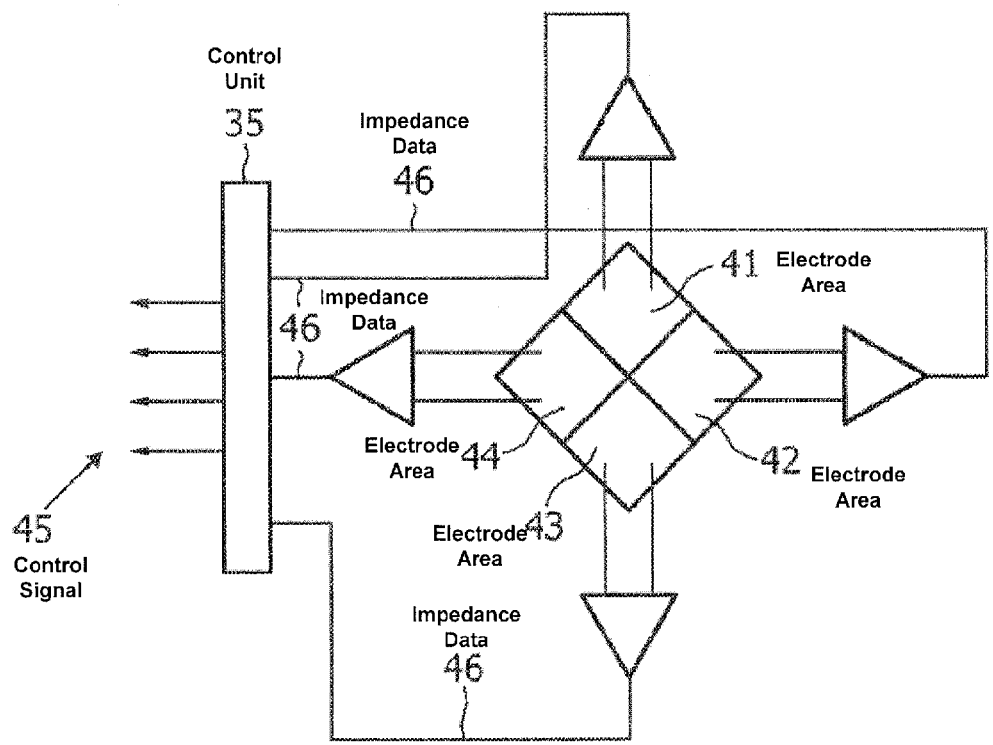
Figure 6:
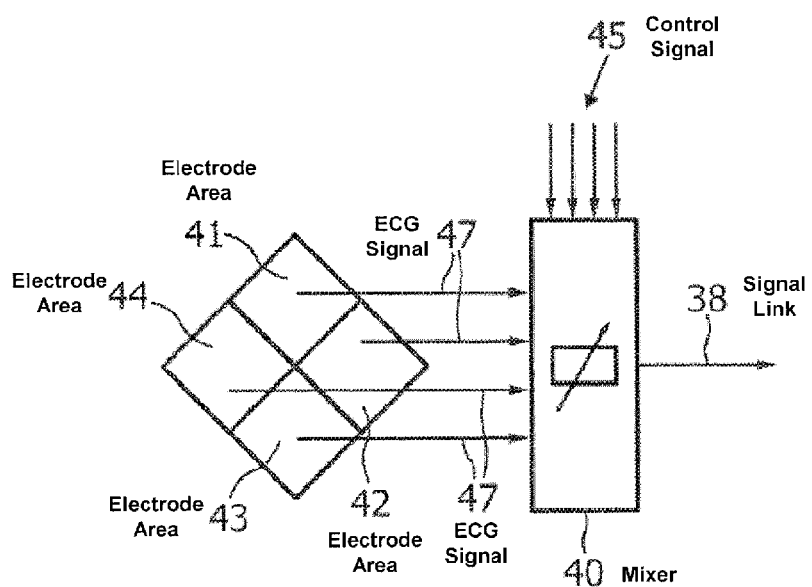

These and other aspects of the invention will be described in detail hereinafter, by way of example, with reference to the following embodiments and the accompanying drawings; in which:

FIG. 1 is a graph of an ECG signal and a graph of an accelerometer signal, both as a function of time, FIG. 2 is a schematic diagram of the system according to a first embodiment, FIG. 3 is a schematic diagram of the system according to a second embodiment, FIG. 4 is a schematic diagram of the system according to a third embodiment, FIG. 5 is a schematic diagram of the determination unit according to the third embodiment, and FIG. 6 is a schematic diagram of the adjusting unit according to the third embodiment.

FIG. 1 illustrates the effect of movement, represented by an accelerometer signal 1, on an ECG signal 2. In a first measuring period 3 the user carrying the ECG electrodes does not move. In this case no accelerometer signal 1 is determined and the ECG shows a clear heart signal. In a second measuring period 4 the user moves. This results in clear disturbances of the ECG signal 2, although in this case the heart rate can still be determined, because of a relative good contact pressure.

An ECG measuring system 10 according to a first embodiment of the invention is illustrated in FIG. 2. The system 10 comprises an ECG electrode 11, a determination unit 12 and an adjusting unit 13. The determination unit 12 is adapted for determining the displacement of an electrode 11, whereas the adjusting unit 13 is adapted for adjusting the position of the electrode 11 depending on the determined displacement.

The determination unit 12 comprises an accelerometer 14, which is positioned in immediate vicinity of the electrode 11. The measured accelerometer data (input signal) are fed into a control unit 15 for generating a control signal (output signal) based on the motion of the user. The control unit 15 uses a computation model for determining the displacement of the electrode 11. The computation model is based upon the correlation between the position where the electrode 11 is mounted on the one hand, and the change of displacement of the electrode 11 due to a movement of the body on the other hand. For example, if the electrode 11 is mounted on the user's chest and the accelerometer data indicate, that the user bends forward, it is very likely that the electrode 11 moves slightly in a specific direction, which can be predicted depending on the acceleration data.

If the analysis of the accelerometer data by the control unit 15 indicates, that the electrode 11 has moved in a specific direction, the control unit 15 generates a control signal for instructing the adjusting unit 13 to move the electrode 11 in it's original position. For analyzing the accelerometer data using the computation model and for generating the control signal the control unit 15 comprises a microprocessor or another data processing means.

The control signal is fed into the adjusting unit 13, which comprises an actuating element 16 for moving the electrode 11 relative to the user's skin based on the electrode displacement determined in a prior step. In this way the position of the electrode 11 is adjusted continuously depending on the movement of the user. The ECG measuring signals of the electrode 11 are transferred via a signal link 18 to an external ECG monitor (not shown).

Preferably electrode 11, control unit 15 and adjusting unit 13 form a integral electrode unit 17 to be mounted on the user's skin.

An ECG measuring system 20 according to a second embodiment of the invention is illustrated in FIG. 3. The system 20 comprises an ECG electrode 21, a determination unit 22 and an adjusting unit 23. The determination unit 22 comprises a first accelerometer 24 and a second accelerometer 29. The first accelerometer 24 is positioned at the electrode 21 such that the first accelerometer 24 and the electrode 21 form an motional unit. The first accelerometer 24 is adapted for determining the displacement of the electrode 21, whereas the second accelerometer 29 is adapted for determining the motion of the user wearing the electrode 21. For this purpose the second accelerometer 29 is positioned in immediate vicinity of the electrode 11.

All accelerometer data (input signal) are fed into a control unit 25 for generating a control signal (output signal) based on the motion of the electrode 21 relative to the user. If the analysis of the accelerometer data by the control unit 25 indicates, that the electrode 21 has moved in a specific direction, the control unit 25 generates a control signal (output signal) for instructing the adjusting unit 23 to move the electrode 21 in it's original position. Because an additional accelerometer 29 is used, more acceleration data is available. Thus, the control unit 25 may use a less complex computation model for determining the displacement of the electrode 21, as it is the case in the first embodiment. For analyzing the accelerometer data using the computation model and for generating the control signal the control unit 25 again comprises a microprocessor or another data processing means.

The control signal is fed into the adjusting unit 23, which again comprises an actuating element 26 for moving the electrode 21 accordingly. Preferably electrode 21, control unit 25 and adjusting unit 23 form a integral electrode unit 27 together with the first accelerometer 24. Again the position of the electrode 21 is adjusted continuously depending on the movement of the user. The ECG measuring signals of the electrode 21 are transferred via a signal link 28 to an external ECG monitor (not shown).

An ECG measuring system 30 according to a third embodiment of the invention is illustrated in FIGS. 4, 5 and 6. The system 30 comprises a determination unit 32 with an ECG electrode arrangement 31 and an adjusting unit 33. The electrode arrangement 31 comprises four isolated electrode areas 41, 42, 43, 44. An impedance distribution is determined by comparing the impedance of the different electrode areas 41, 42, 43, 44 (input signal) by a control unit 35. For this purpose the electrode arrangement 31 is adapted such that it allows impedance measuring. The control unit 35 generates a control signal 45 (output signal) by applying a computation model to the impedance data 46. For analyzing the impedance data 46 and for generating the control signal 45 the control unit 35 comprises a microprocessor or another data processing means, e.g. a signal processor. The control signal comprises an instruction for the adjusting unit 33. The instruction depends on the displacement of the electrode characterized by a change in the impedance distribution over the electrode areas 41, 42, 43, 44.

At the same time the four electrode areas 41, 42, 43, 44 provide ECG measuring signals 47 to the adjusting unit 33. The adjusting unit 33 comprises a mixer 40, e.g. a signal processing unit, adapted for weighting the ECG measuring signals 47 according to the control signal 45. In other words the virtual measuring position of the electrode arrangement 31 is adjusted according to its displacement.

If the user does not move, each electrode area 41, 42, 43, 44 contributes similarly to the impedance distribution. If the position of the electrode arrangement 31 relative to the user's skin changes because the user moves, the "normal" impedance distribution changes towards a "dynamic" impedance distribution. For example a first electrode area 41 contributes 80 percent and the other three electrode 42, 43, 44 areas together contribute 20 percent of the impedance. Then there is a strong indication that the electrode arrangement 31 has moved towards the first electrode area 41. In this case the control signal is generated such that the mixer 40 mixes the incoming ECG measuring signals 47 in a way that 20 percent of the measuring signals from the first electrode area 14 is mixed with 80 percent of the measuring signals from the three other electrode areas 42, 43, 44. In other words, the virtual measuring position of the electrode arrangement 31 is adjusted depending on the movement of the user. This is achieved by aiming for a uniform impedance distribution over all four electrode areas 41, 42, 43, 44. The resulting ECG measuring signals of the electrode arrangement 31 are transferred via a signal link 38 to an external ECG monitor (not shown). Preferably electrode arrangement 31, control unit 35 and adjusting unit 33 form a integral electrode unit 37.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit may fulfil the functions of several means recited in the claims. Any reference signs in the claims shall not be construed as limiting the claim concerned.

REFERENCE LIST 1 accelerometer signal
2 ECG signal
3 first measuring signal
4 second measuring signal
10 measuring system
11 electrode
12 determination unit
13 adjusting unit
14 accelerometer
15 control unit
16 actuating element
17 electrode unit
18 signal link
20 measuring system
21 electrode
22 determination unit
23 adjusting unit
24 first accelerometer
25 control unit
26 actuating element
27 electrode unit
28 signal link
29 second accelerometer
30 measuring system
31 electrode arrangement
32 determination unit
33 adjusting unit
35 control unit
37 electrode unit
38 signal link
41 electrode area
42 electrode area
43 electrode area
44 electrode area
45 control signal
46 impedance data
47 ECG signal

The invention claimed is:

1. A method of measuring bioelectrical signals of a user, comprising the steps of:
continuously determining the displacement of an electrode, the electrode being adapted for measuring a bioelectrical signal, and
continuously adjusting, during the measuring of the bioelectrical signal, the position of said electrode depending on the determined displacement,
wherein the displacement is determined using a first accelerometer and a second accelerometer, the first accelerometer determining the motion of the electrode and the second accelerometer determining the motion of the user.

2. The method as claimed in claim 1, wherein the determining step comprises determining the motion of the electrode relative to the user.

3. The method as claimed in claim 1, wherein the adjusting step comprises adjusting the real position of the electrode.

4. The method as claimed in claim 1, wherein the adjusting step comprises adjusting the virtual measuring position of the electrode.

5. A system for measuring bioelectrical signals of a user, comprising:
- a determination unit adapted for continuously determining the displacement of an electrode, the electrode being adapted for measuring a bioelectrical signal, and
- an adjusting unit adapted for continuously adjusting, during the measuring of the bioelectrical signal, the position of said electrode depending on the determined displacement,
- wherein the determination unit includes a first accelerometer and a second accelerometer, the first accelerometer determining the motion of the electrode and the second accelerometer determining the motion of the user.

6. The system as claimed in claim 5, wherein the second accelerometer is arranged remotely from the electrode.

7. The system as claimed in claim 5, wherein the first accelerometer and the electrode form a motional unity.

8. The system as claimed in claim 5, wherein the adjusting unit comprises an actuating element for moving the electrode.

9. The system as claimed in claim 5, wherein the determination unit further comprises the electrode, said electrode comprising a number of adjacent electrode areas, each area being adapted for measuring a bioelectrical signal.

10. The system as claimed in claim 5, wherein the adjusting unit comprises an analyzing unit adapted for analyzing a number of bioelectrical signals and further adapted for adjusting the virtual measuring position of the electrode.

11. A computer program embodied on a memory of a computer, comprising:
- computer program instructions to continuously determine the displacement of an electrode depending on an input signal, the electrode being adapted for measuring a bioelectrical signal, and
- computer program instructions to generate an output signal for continuously adjusting, during the measuring of the bioelectrical signal, the position of said electrode depending on the determined displacement, when the computer program is executed in a computer,
- wherein the computer program instructions determine the displacement using first signals from a first accelerometer and second signals from a second accelerometer, the first signals indicating the motion of the electrode and the second signals indicating the motion of the user.

* * * * *